United States Patent [19]

Liu

[11] Patent Number: 4,542,653
[45] Date of Patent: Sep. 24, 1985

[54] APPARATUS AND METHOD FOR BEAMFORMING IN AN ULTRASONIC TRANSDUCER ARRAY

[75] Inventor: Ren-Young Liu, Mesa, Ariz.

[73] Assignee: Advanced Technology Laboratories, Inc., Bothell, Wash.

[21] Appl. No.: 554,017

[22] Filed: Nov. 21, 1983

[51] Int. Cl.$^4$ .............................................. G01N 29/00
[52] U.S. Cl. ..................................... 73/626; 128/660; 367/105; 367/905
[58] Field of Search ............... 73/609, 617, 625, 626, 73/628; 128/660; 367/105, 905

[56] References Cited

U.S. PATENT DOCUMENTS

| | | | |
|---|---|---|---|
| 3,936,791 | 2/1976 | Kossoff | 73/626 X |
| 4,180,790 | 12/1979 | Thomas | 73/626 |
| 4,208,916 | 6/1980 | Thomenius et al. | 73/626 |
| 4,334,432 | 6/1982 | Gill | 73/625 |
| 4,458,533 | 7/1984 | Borburgh | 73/625 |

*Primary Examiner*—Stewart J. Levy
*Assistant Examiner*—John E. Chapman, Jr.
*Attorney, Agent, or Firm*—Lawrence S. Levinson; Robert E. Lee, Jr.

[57] ABSTRACT

Electronically changing the effective element spacing of an array of acoustic transducer elements between the transmit and receive modes of operation of an ultrasound apparatus results in reducing the deleterious effects of grating lobes present in the pattern of the array because of element spacings in excess of one half of a wavelength. A linear or quadratic time delay distribution, or both simultaneously, is applied to the array for scanning and/or focusing by setting individually the time delay of the energy associated with each element of the array during one mode of operation, e.g. transmit. The array is organized into groups of elements, e.g. pairs, and the time delay distribution is applied by setting the time delay of the energy associated with each group of the array during the remaining mode of operation, e.g. receive.

6 Claims, 6 Drawing Figures

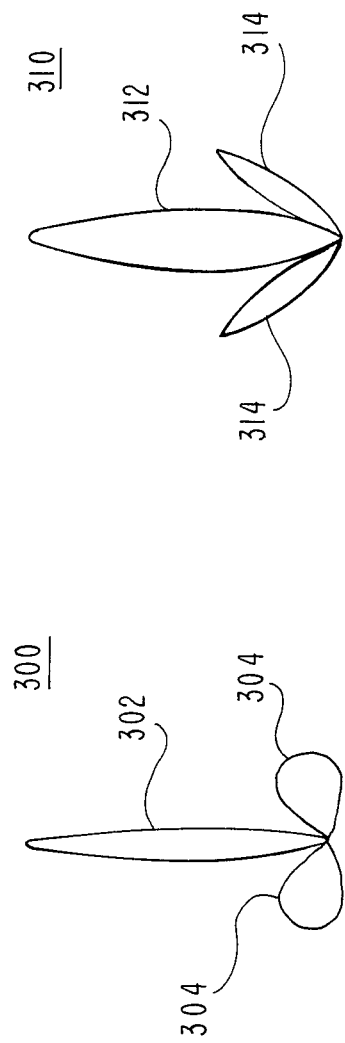
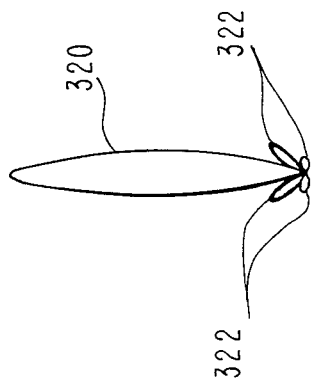
Fig. 3a  Fig. 3b  Fig. 3c

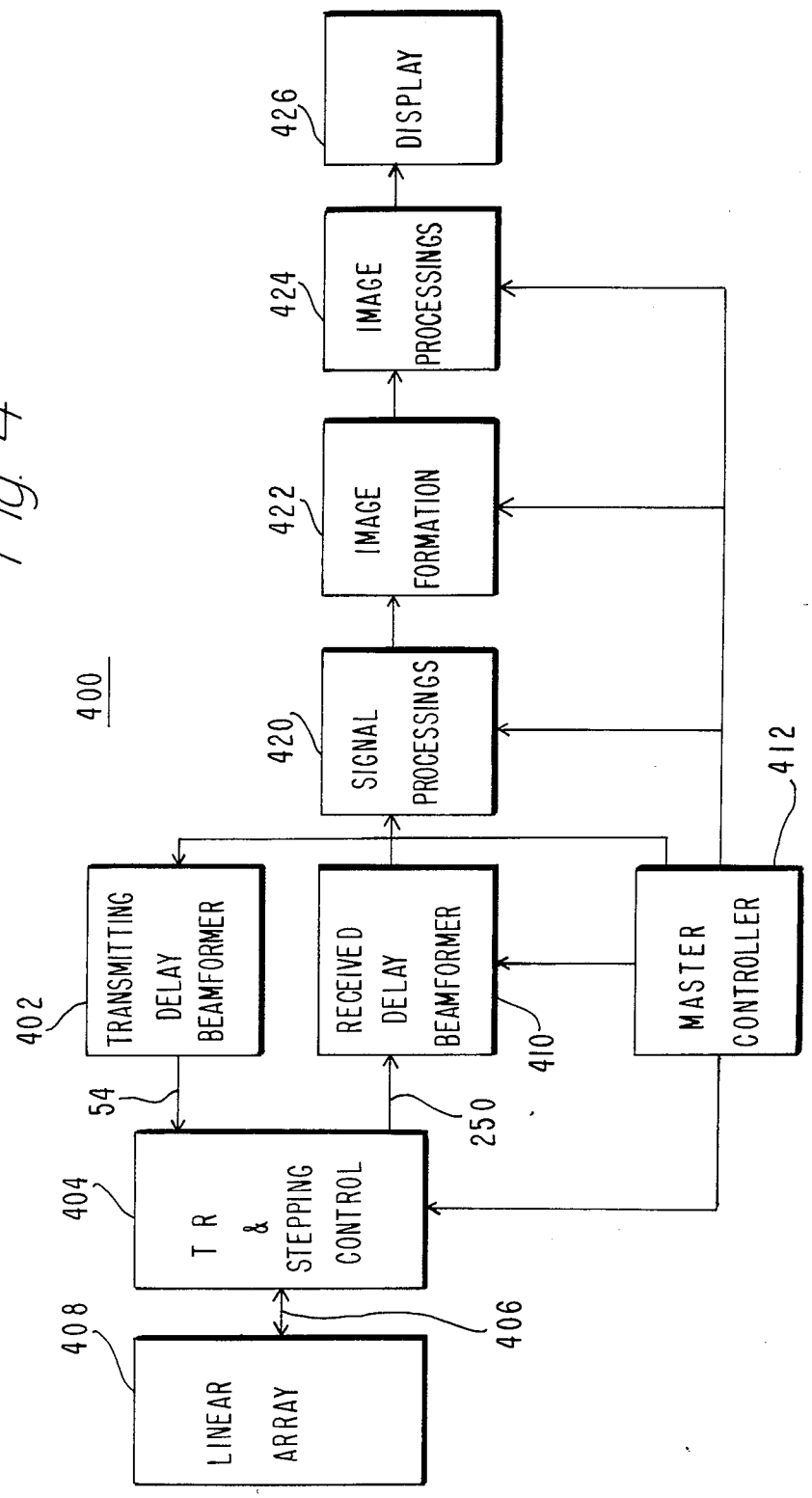

APPARATUS AND METHOD FOR BEAMFORMING IN AN ULTRASONIC TRANSDUCER ARRAY

BACKGROUND OF THE INVENTION

The present invention relates to ultrasound devices. In particular, it relates to transducer arrays used in medical ultrasound diagnostic equipment.

Medical ultrasound diagnostic equipment use short pulses of ultrahigh frequency acoustic energy to examine tissues of the body. Ultrasound pulses traveling through the body are reflected and scattered by tissue density and elasticity changes. These reflections are detected and plotted in various ways to provide an image of internal body regions such as organs, etc.

Piezoelectric transducers are used to produce beams of ultrasonic energy and to detect the reflections or echoes. In order to complete the image of the desired bodily region under investigation, the beam is scanned. This can be done automatically using either mechanical or electronic scanning. Electronic scanning includes: switching among elements or portions of elements in a linear array; or angular scanning of the beam in a phased array.

Linear arrays or phased arrays provide an opportunity to control the phasing of each element contributing to the pattern response of the array. This in turn provides some degree of control over the shape of the pattern. Phase control allows a designer to focus the beam and electronically scan it. Because of the electronic control, errors are partially compensated for, and the use of mechanical parts and assemblies can be eliminated.

Prior art examples of acoustic transducer arrays are:

U.S. Pat. No. 3,936,791 wherein a linear array of transducer elements is utilized to provide electronic focusing in the longitudinal plane of the array and mechanical focusing in the plane perpendicular to the longitudinal plane;

U.S. Pat. No. 4,180,790 which relates to an electronically controlled aperture wherein the size of the aperture and the focus of the aperture can be dynamically controlled; and U.S. Pat. No. 4,334,432, which relates to providing linear and quadratic time delay distributions to an array of acoustic transducers in order to provide scan and focusing capabilities.

One common problem encountered with prior art linear and phased arrays is the presence of grating lobes. These arise as redundant or secondary beams in the pattern of the array. In a linear or phased array the time delay associated with energy transmitted or received by each element of the array is not necessarily the same. A time delay distribution across the aperture of the array results in a main beam being formed in the pattern. Depending on the number of elements of the array, the spacing of the elements and the time delay distribution, the beam width of the main beam and the level of the side lobes can be controlled to a considerable extent. However, if the spacing between elements in the array exceeds one half of a wavelength at the operating frequency of the array, then the presence of unwanted secondary beams called grating lobes, which are not as large as the main beam, but which may exceed the average side lobe level, are automatically formed. Grating lobes occur because of the geometry involved in the transducer array.

Because of grating lobes, errors and noise are introduced into the ultrasound imaging or scanning process. Although the main beam is directed at a particular spot of the target area at a given instant in time, the contributions to the return echo include reflections caused by the grating lobes looking at different spots. Hence, the image is smeared by the several contributions. It is, therefore, highly desirable to reduce or eliminate grating lobes. One manner of doing this is to reduce the spacing between array elements to less than one half wavelength at the operating frequency. However, to maintain the same aperture size as arrays with multiple wavelength spacing, one half wavelength arrays would require additional channels which in turn would result in greater expense. Typical transducer element spacings fall between one half and five wave lengths.

SUMMARY OF THE INVENTION

An object of the present invention is to provide an improved apparatus and method for ultrasound scanning.

A further object of the present invention is to provide an apparatus and method for reducing the effect of grating lobes in the pattern response of an acoustic transducer array used in ultrasound scanning.

According to the invention, the effective spacing of the elements of a transducer array are changed electronically between the transmit and receive modes of operation of the array. This is accomplished by organizing the array into adjacent groups of elements; providing a time delay distribution to the array by adjusting the time delay of the response of each element of the array during one mode of operation; and applying a time delay distribution to the array by adjusting the delay of the response of each group of elements within the array.

One time delay distribution applied to the array comprises a quadratic time delay distribution whereby focusing of the array takes place. Further, a time delay distribution comprising applying a linear time delay distribution simultaneously with said focusing quadratic time delay distribution is applied to the array whereby linear scanning of the pattern of the array takes place.

Further, in accordance with this invention, an ultrasound imaging apparatus is provided which includes an array of acoustic transducer elements for providing both transmit and receive functions. The ultrasound imaging apparatus is provided with means for applying a time delay distribution to the array of elements and means for electronically changing the effective spacing of the elements between the transmit and receive stages of operation of the array. The means for electronically changing the effective spacing of the array further comprises means for forming adjacent groups of elements within the array. The spacing between adjacent elements in the array is between one half wave length and five wave lengths.

BRIEF DESCRIPTION OF THE DRAWINGS

In the drawings:

FIGS. 3(a)-(b) illustrate the patterns of the transducer arrays of FIGS. 1 and 2 respectively, while FIG.

3(c) illustrates the pattern produced by multiplying the patterns of FIGS. 3(a) and (b) together.

FIG. 4 is a block diagram of an ultrasound scanning system including the present invention.

DETAILED DESCRIPTION OF THE INVENTION

Figure 1:
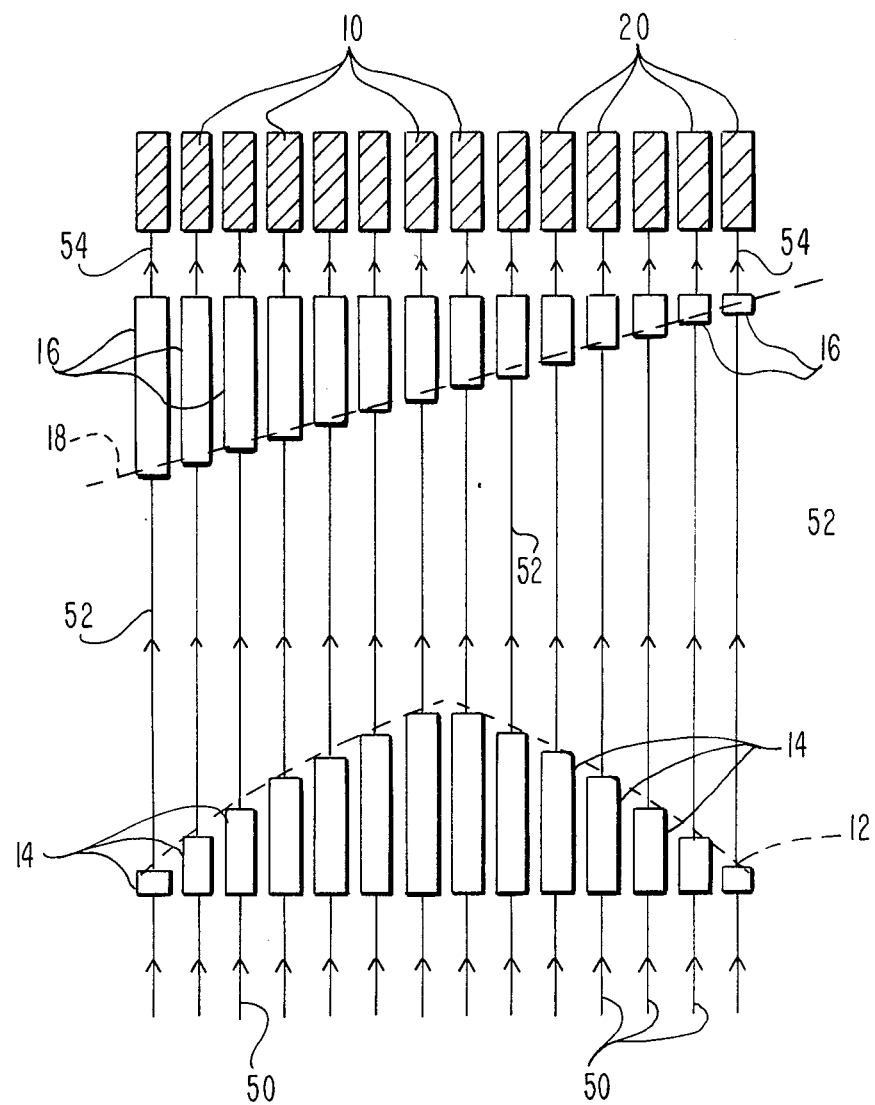
FIG. 1 is a first schematic of a transducer array having steering and focusing time delays applied thereto.

Referring to FIG. 1, an array of acoustic transducer elements 10 is shown. Each of the acoustic transducers, made of a material having piezoelectric properties, will convert electrical energy applied thereto into acoustic energy or convert acoustic energy impinging thereon into electrical energy. Each transducer will propagate acoustic energy or receive it in accordance with a transducer pattern. The pattern is a measure of the sensitivity of the response of the transducer to acoustic energy (both in transmit and receive) vs. angle of rotation about the transducer.

In an array of transducers the combined effect of the transducer elements will result in a single combined transducer array pattern. By controlling the activations of the transducers in the array and the spacing of the transducer elements, the pattern can be significantly controlled and shaped. Controlling the activations means controlling the time delay of the response of each element of the array relative to a reference element in the array, for example, the center element or one of the end elements.

The term transducer array as used herein refers to both linear arrays and phased arrays. Typically, a transducer array is formed from a single piece of piezoelectric material having, for example, parallel front and back faces. The back face is segmented into an array of transducer areas by cutting a series of equidistant parallel lines therein. Electrical connections are made individually to each area. Acoustical energy is propagated from the front face and received therefrom in accordance with the electrical connections made to the segmented areas on the back face. Alternatively, a transducer array is one in which each element of the array is a separate transducer with individual electrical connections made to each transducer.

Typically, the desired pattern of a transducer or array of transducers includes a main beam with low side lobes. Because of the low side lobes most of the energy launched into the body tissue is along a single scan line in line with the main beam. If the side lobes are too high, energy will also be transmitted into the body tissue along several different directions associated with the position of the sidelobes, and returns from the different directions will be received by the transducer or transducer array along with reflections from along the selected scan line causing errors.

Because the target areas are often relatively close to the transducer it becomes necessary to focus the beam of the transducer to concentrate acoustic energy on the target area. Focusing is accomplished with a transducer array by applying a symmetrical time delay distribution to the array of transducers 10 in FIG. 1 (see the dashed line 12). For example, the response of the transducer elements at either end of the array are delayed the least or not at all while the transducer elements closer to the center are progressively delayed more and more until the maximum time delay is obtained at the center. One well known focusing time delay distribution is the quadratic distribution in which the time delay for each element decreases non-linearly as the distance of the element from the center element. This is the focusing time delay distribution depicted by the dashed line 12.

Time delays are denoted by the blocks 14 in FIG. 1. They are shown longer for longer time delays and shorter for shorter time delays. There are a number of well known devices for implementing acoustic time delays, for example, charged coupled devices (CCD), or tapped delay lines. In the preferred embodiment of this invention, tapped delay lines were used.

Also shown in FIG. 1 is a second set of time delays 16 which are used to implement a second time delay distribution to the array of elements 10. In FIG. 1 the time distribution displayed by the time delay devices 16 is a linear time delay distribution. The delay on the left most transducer element is greatest while that of the right most element is least with the time delay of the intermediate elements decreasing linearly from left to right. It is well known that by using a linear time delay distribution the main beam of the array pattern will point in a direction perpendicular to the phase front of the linear array shown by the dashed line 18. If equal time delays are applied to all of the array elements, then the main beam points in a direction perpendicular to the front face of the array formed by the front edges 20 of the aligned transducer elements 10. As the slope of the dashed line 18 changes in accordance with the change in the linear time delay distribution the main beam rotates and points in a direction forming an angle $\Theta$ from the normal to the array front.

FIG. 3(a) shows a depiction of a typical transducer array pattern 300 where the element spacing of the array exceeds $\lambda/2$. The pattern includes a main beam 302 and grating lobes 304. In FIG. 3(a) the main beam is pointed in a direction of $\Theta = $ zero degrees which is normal to the array front.

Figure 2:
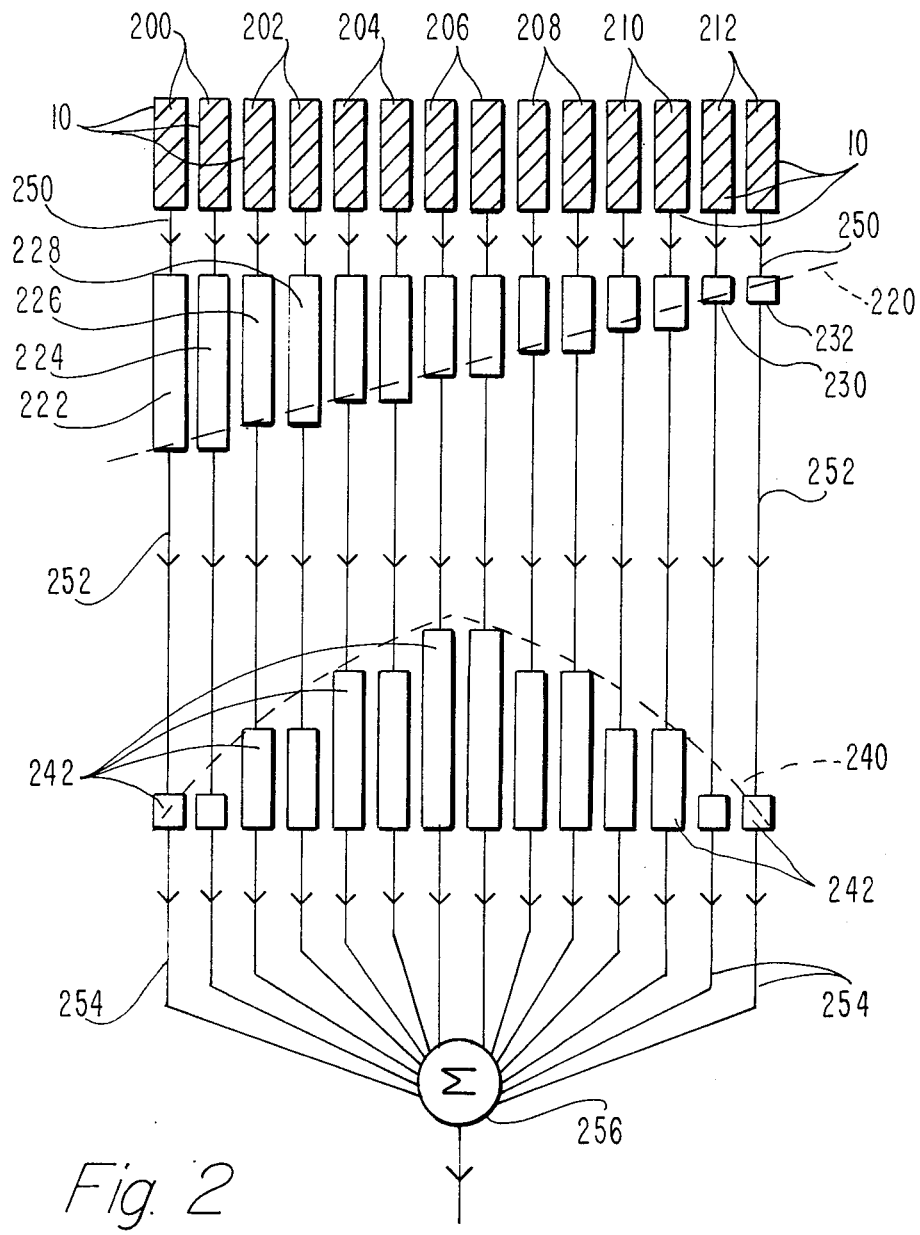
FIG. 2 is a second schematic of the transducer array of FIG. 1 having steering and focusing time delays applied thereto.

FIGS. 1 and 2 both show an array of fourteen acoustic transducer elements 10. More or less elements could be used, but for purposes of illustration here, only fourteen were chosen. In FIG. 2, the fourteen elements are organized into seven pairs of elements, even numbers 200 through 212. When applying a linear time delay distribution as depicted by the dashed line 220 in FIG. 2 to the adjacent pairs of elements, equal time delays are applied to each element in a pair. For example, the time delay applied by time delay devices 222 and 224 are equal and are being applied to the acoustic transducer elements of pair 200. The next pair of time delay devices 226 and 228 apply equal time delays to the transducer pair 202. The time delay applied to pair 202 is less than that applied to pair 200. This continues in linear fashion until the least amount of time delay is applied to pair 212 by the time delay devices 230 and 232.

Similarly, a focusing quadratic time delay distribution (dashed line 240) is applied to the transducer pairs even numbers 200–212 by time delay devices 242 by applying equal time delays to each element of a transducer pair, but by changing the amount of delay applied to adjacent pairs.

By applying equal time delays to each element of a pair, the effective spacing of the array is changed. Effectively, when using paired groups of elements, the spacing is doubled. Other groupings could be used, for example, groupings of three or four or five elements, but for purposes of illustration, pairs of elements were used. Because the effective element spacing is now changed, the pattern of the array changes, including the size and angular direction of the grating lobes. See pattern 310 of FIG. 3(b). Note that the main beam 312 of pattern 310 is broader than main beam 302 of FIG. 3(a) and the grating lobes 314 are a different shape with a different angular orientation. The grating lobes of pattern 310 occur at a lesser angle with respect to the center line of the main beam 312. In fact, angular occurrence of grating lobes can be predicted in the continuous wavecase, by knowing the wave length and spacing as follows:

$$\Theta = \sin^{-1} \lambda/S$$

where $\Theta$ is the angle which the grating lobe makes with the normal to the array: $\lambda$ is the acoustical wave length in the propagating medium and S is the element spacing.

In typical ultrasonic imaging or scanning devices with linear arrays, triggering pulses are applied to the elements of the transducer array causing a beam of acoustic energy to be transmitted into the object under investigation for a short duration of time along a particular scan line. See for example pattern 300. Then a period of waiting occurs until the energy propagates into the tissue and encounters points of reflection along the chosen scan line at which time reflection echoes are formed and reflected back toward the transducer array where they are detected in accordance with the pattern of the array and converted into electrical signals. The narrow main beam 302 is desirable in the pattern in order to obtain good lateral resolution between scan lines. However, some scattered energy will be generated and detected by the grating lobes 304. However, if the pattern on receive is changed from that used on transmit such that the position of the transmit and receive grating lobes are different, then it is possible to bias against reception by receive pattern grating lobes of reflected energy caused by transmit pattern grating lobes.

The overall pulse echo pattern of the array is actually a multiplicative combination of the transmit and receive patterns. If a null is present in the receive pattern where a peak of a grating lobe is present in the transmit pattern then a null will be present in the combined pulse echo pattern. Similarly, if a low level is present in the transmit pattern where a high level grating lobe is present in the receive pattern then only a low level will be present in the combined pattern. Since the peak of the main beam is present at substantially the same location in both the receive and transmit patterns, then the peak of the main beam in the pulse echo pattern is not destroyed. However, since the effective spacing of the elements in the receive pattern is greater there is an effect on the main beam shaping. Usually the main beam becomes broader as is demonstrated by comparing the main beam 320 of the combination pulse echo pattern of FIG. 3(c) with the patterns in FIGS. 3(a) and 3(b). Hence, the combination main beam 320 is broader than the transmit beam and narrower than the receive beam. In pattern 3(c) the effective grating lobes 322 are quite small. Had a three element or four element grouping been tried, the effect on the main beam would probably be greater. Also, the degree of success in using the teaching of this invention depends on the frequency of operation and the size and spacing of the elements. It is most advantageous when the nulls of one pattern are located where the peaks of the grating lobes occur in the other pattern, and vice versa.

FIG. 1 is arranged to show the transmitting delay beamformer where individual electrical triggering input lines 50 are coupled to time delay devices 14 which in turn are coupled by lines 52 to time delay devices 16. Time delay elements 16 are coupled to transducer elements 10. by lines 54. FIG. 2 shows the received delay beamformer where acoustical transducer elements 10 are coupled electrically to time delay devices 226, 228, etc. by individual lines 250 which in turn are coupled to the delay devices 242 via lines 252. Time delay devices 242 are in turn coupled to a summer circuit 256 by individual lines 254. The receive channels are separated from the transmit channels by a transmit/receive switch not shown in FIGS. 1 or 2.

Referring now to FIG. 4, a block diagram schematic of an ultrasound scanner designated generally 400 is shown. The electrical triggering pulses are generated within the transmitting delay beamformer 402 described above in detail in connection with FIG. 1. The output signals of beamformer 402 pass via multiple lines 54 through transmit/receive switch 404 to be coupled via multiple lines 406 to a plurality of transducer elements in the linear array 408. On receive the electrical signals from the transducer elements of the linear array travel through transmit/receive switch and then via multiple lines 250 to the received delay beamformer 410 described above in more detail in connection with FIG. 2. The amount of delay attributed to each transducer array element on either transmit or receive is controlled automatically by the master controller 412. It is possible to have the same set of transmit delay devices act as both transmit and receive time delay devices with the controller 412 changing and setting the delays between each transmit and receive cycle. Master controller 412 also controls the transmit/receive switch 404.

In the preferred embodiment of this invention, the time delay devices 16 of FIG. 1 are used as time-delay devices 222, 224 etc. of FIG. 2 and the time delay devices 14 of FIG. 1 are used as the delay devices 242 of FIG. 2.

The received signals after passing through the receive delay beamformer 410 are further processed for display as an ultrasonic image in any number of conventional well-known ways. In FIG. 4, the signals are shown being pre-processed in a signal processing step 420; an image is formed from the pre-processed signals and further processed in steps 422 and 424; and then the image is displayed on a display 426. These steps are accomplished under the control of the master controller 412. Implementation of blocks 420–426 are well-known and a detailed description herein is not necessary for an understanding of the present invention. In the preferred embodiment, a 64 element linear transducer array with 2 mm spacing operating at approximately 3.5 MHz was used. Only eight elements at a time are activated and scanning takes place by switching the eight active elements along the 64 element array. This can be accomplished in switch 404 under the control of controller 412 in FIG. 4. Hence, no linear time delay was utilized. However, a quadratic focusing time delay distribution was applied to the eight element array. When the transmit and receive patterns were kept the same the return signals due to the grating lobes were clearly present on the display of an ADR 4000 scanner. However, when the receive pattern was changed in accordance with teachings of this invention, that is, the array now comprised four pair of two elements each instead of eight individual elements, the ghosts disappeared.

While the invention has been described with reference to the figures, it will generally be understood by those skilled in the art that various changes may be made and equivalents be substituted for elements thereof without departing from the true spirit and scope of the invention.

What is claimed is:

1. The method of reducing the effects of grating lobes in the pattern of an array of acoustic transducer elements comprising:
    changing electronically the effective spacing of the elements in the array between the transmit and receive modes of operation, the step of changing the effective spacing comprising:
    organizing the array into adjacent groups of elements;
    applying a time delay distribution comprising a beam steering linear distribution simultaneously with a focusing quadratic distribution to the array by setting a time delay for the energy associated with each element during one mode of operation; and
    applying said time delay distribution to the array by setting a time delay for the energy associated with each group during the remaining mode of operation, the time delay for each element in a group being the same.

2. An ultrasound apparatus including an array of acoustic transducer elements for providing both transmit and receive functions for said ultrasound apparatus comprising:
    means for applying simultaneously a beam steering linear time delay distribution and quadratic focusing time delay distribution to said array of elements; and
    means for electronically changing the effective spacing of said elements between transmit and receive functions whereby the grating lobe levels of the pattern of said array are lowered, said means for changing comprising:
    means for forming adjacent groups of said elements with each group comprising at least two elements; and
    means for applying simultaneously a linear time delay distribution and a quadratic focusing time delay distribution to said groups of elements, the time delay to each element in a group being the same.

3. The apparatus of claim 2 wherein the spacing between adjacent elements in said array is equal to or exceeds $\frac{1}{2}\lambda$.

4. The method of reducing the effects of grating lobes in the pattern of an array of acoustic transducer elements comprising:
    changing electronically the effective spacing of the elements in the array between the transmit and receive modes of operation, the step of changing the effective spacing comprising:
    organizing the array into adjacent groups of elements;
    applying a beam steering time delay distribution to the array by setting a time delay for the energy associated with each element during one mode of operation; and
    applying the beam steering time delay distribution to the array by setting a time delay for the energy associated with each group during the remaining mode of operation, the time delay set for each element in group being the same.

5. An ultrasound apparatus including an array of acoustic transducer elements for providing both transmit and receive functions for said ultrasound apparatus comprising:
    means for applying a beam steering time delay distribution to said array of elements; and
    means for electronically changing the effective spacing of said elements between transmit and receive functions whereby the grating lobe levels of the pattern of said array are lowered, said means for changing the effective spacing comprising:
    means for forming adjacent groups of said elements with each group comprising at least two elements; and
    means for applying a beam steering time delay distribution to said groups of elements, the time delay to each element in a group being the same.

6. The apparatus of claim 5 wherein the spacing between adjacent elements in said array is greater than one half wavelength.

* * * * *